US00PP23759P3

(12) United States Plant Patent
Zwetzig

(10) Patent No.: US PP23,759 P3
(45) Date of Patent: Jul. 23, 2013

(54) ***HIBISCUS* PLANT NAMED 'SATELLITE'**

(50) Latin Name: ***(Hibiscus moscheutos*×*H. coccineus)*×TH 56**
Varietal Denomination: Satellite

(75) Inventor: Gretchen Zwetzig, Lindsay, CA (US)

(73) Assignee: Gretchen Zwetzig, Lindsay, CA (US)

( * ) Notice: Subject to any disclaimer, the term of this patent is extended or adjusted under 35 U.S.C. 154(b) by 149 days.

(21) Appl. No.: 12/932,349

(22) Filed: Feb. 25, 2011

(65) Prior Publication Data

US 2012/0222175 P1 Aug. 30, 2012

(51) Int. Cl.
*A01H 5/00* (2006.01)

(52) U.S. Cl.
USPC ..... Plt./257

(58) Field of Classification Search
USPC ..... Plt./257
See application file for complete search history.

*Primary Examiner* — June Hwu

(57) ABSTRACT

A new and distinct cultivar of winter hardy *Hibiscus* plant named 'Satellite' is the result of a unique hybridization. This new and distinct cultivar is characterized primarily as to its novelty by its extreme cold hardiness to Zone 4, medium to large, thick-textured, reddish to mauve colored flowers and its shiny, petite 'maple-shaped' leaves with a purple cast, compactness of about 2 feet, its vigorous and uniform growth habit and its floriferous nature from midsummer until frost.

2 Drawing Sheets

Latin name: (*Hibiscus moscheutos*×*H. coccineus*)×TH56. Varietal denomination: 'Satellite', hardy *Hibiscus*.

FIELD OF THE INVENTION

This plant, as a hybridized hardy *Hibiscus*, is valuable to the landscape market for its improvements in thicker textured and uniquely colored flowers and buds, refined petite "maple-like" foliage of a purple cast, its all-around vigor, compact breaking action, and adaptation to extreme environments, including the ability to consistently survive winter temperatures of at least −30 degrees Fahrenheit.

BACKGROUND OF THE NEW PLANT

The new plant of this invention is the result of a unique hybridization, with the breeding achievement being evidenced in the outstanding combination of characteristics exhibited by this new and distinct *Hibiscus* plant, which are:

(a) Small refined, 3-5 lobed glaborous 'maple-shaped' leaves with a purple cast and relatively smooth margins which combined compliments the landscape;
(b) Medium-sized flowers that are outstanding for their luminescent reddish-mauve colored, thick textured petals;
(c) The plant being very floriferous with flowers that stay open for at least one full day, sometimes up to 2 days;
(d) The plant being small to medium-sized but vigorous with compact and uniform breaking action which gives it unique landscape utility; and
(e) The plant being so hardy that it can consistently withstand winter temperatures of at least −30 degrees Fahrenheit.

SUMMARY OF THE INVENTION

'Satellite' was the result of a 50-year breeding program. Its ancestry includes *H. moscheutos* , *H. coccineus* and *H. rosa*

*sinensis*. More specifically, the plant resulted from multiple crossings with an unnamed, Fleming-bred *H. moscheutos*×*H.coccineus*(non patented) and 'TH-56' a Fleming-bred cross between *H. moscheutos*×*H. rosa sinensis* (non patented). The seedling which most nearly met all of the above standards was selected.

This new plant first bloomed in the summer of 2001 and was selected by Gretchen Zwetzig on her property located at 8101 S. 14th St. Lincoln, Nebr. 68516. Asexual propagation of the plant by cuttings and root division in Lincoln, Nebr. has shown that the unique and distinguishing features of the plant are faithfully transmitted from generation to generation and appear to be fixed.

Since its origin, the plant has bloomed from midsummer until frost, while exhibiting the aforementioned distinctive characteristics. This hardy *Hibiscus* plant greatly contributes to the market with its, remarkable beauty and utter refinement, its compact growth habit, its enhanced resistance to disease and insects, its stability through extremes in rain and drought, and its extreme hardiness.

BRIEF DESCRIPTION OF THE DRAWINGS

The flower and foliage of the cultivar are shown at 2½ years in the attached photographs.

More specifically.

Figure 1:
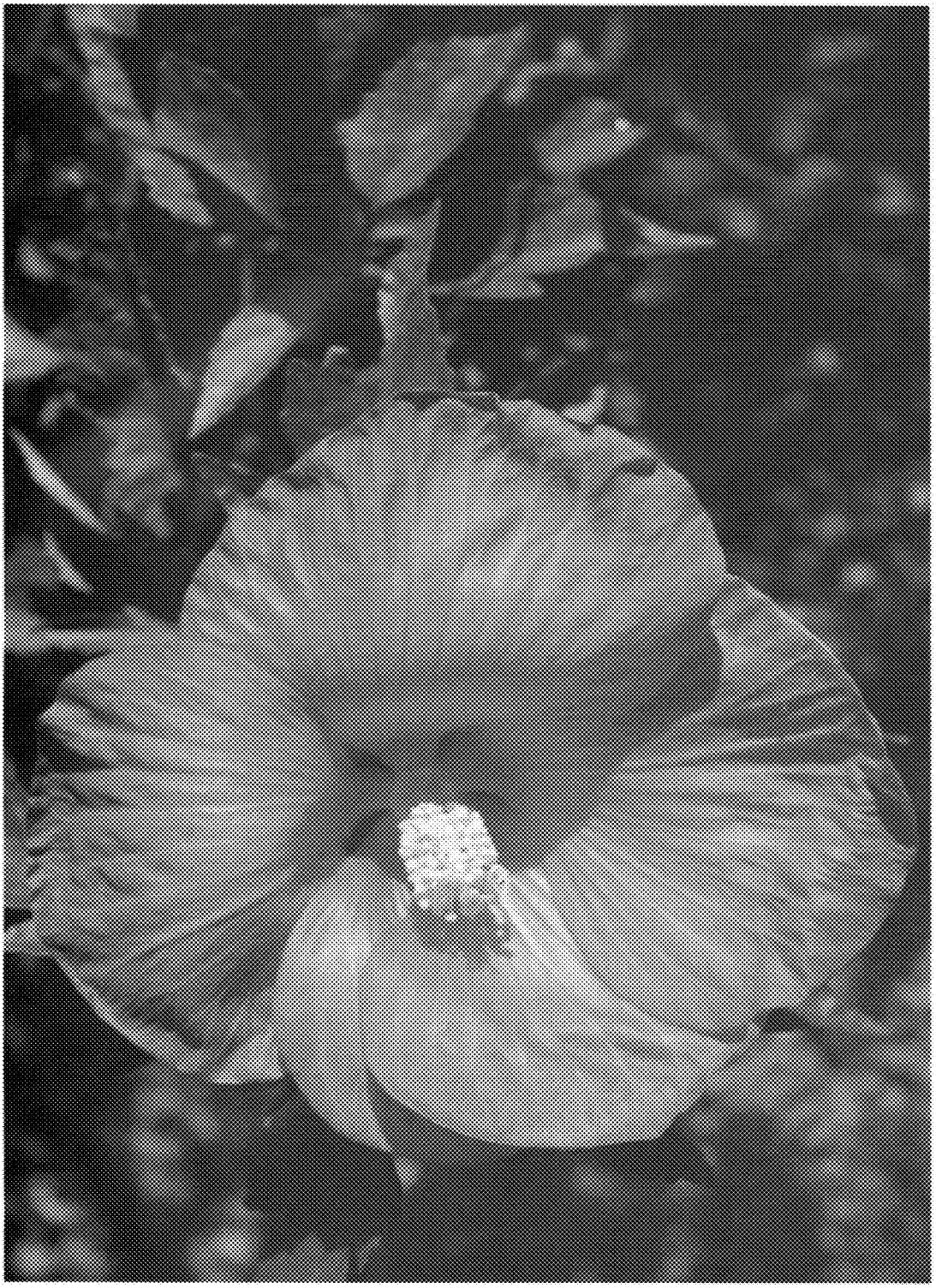
FIG. 1 is a close-up of the flower and the leaf.
Figure 2:
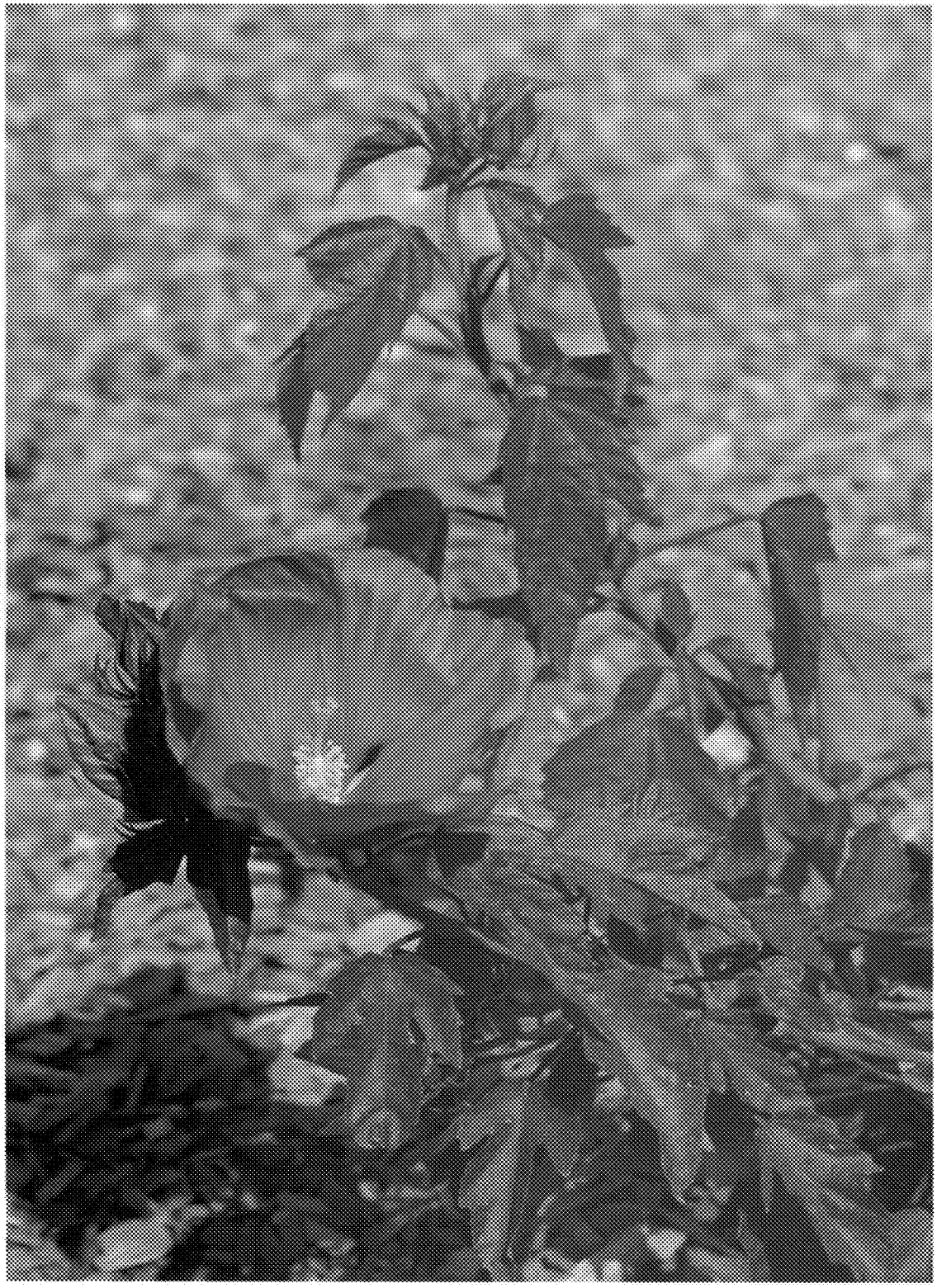
FIG. 2 is a depiction of plant stature.

The colors are as true as is reasonably possible to attain in photographic illustrations of this type. The colors illustrated may be slightly off due to light reflectance.

DESCRIPTION OF THE NEW PLANT

What follows is a detailed description of the new cultivar. The specific color descriptions are in accordance with The Royal Horticultural Society Colour Chart (2001), while general color recitations are consistent with ordinary American terminology.

'Satellite' has not been observed under all possible environmental conditions. It is to be understood that the phenotype may vary significantly with variations in the environment such as temperature, light intensity, humidity, and day length without, however any difference in genotype of the plant. The following botanical characteristics and observations are gathered from the plant when grown in Lincoln, Nebr. (USDA Zone 4).

THE PLANT

Parentage:

*Seed parent.*—*Hibiscus moscheutos*×*Hibiscus coccineus* unnamed and unpatented Fleming-bred seedling.

*Pollen parent.*—*Hibiscus moscheutos*×*Hibiscus rosa sinensis* unnamed and unpatented Fleming seedling.

Comparison between observed plant and parents: Observed Plant is almost 2 feet shorter than parents.

Comparison between observed plant and other known cultivars: Observed Plant is unique, but most similar to: 'Angelique' U.S. Plant Pat. No. 13,734, 'Cherub' U.S. Plant Pat. No. 16,669 and 'Pink Comet' U.S. Plant Pat. No. 13,751 and our other hardy *Hibiscus* in that:

(a) They are all compact at approximately 3 feet on average.

(b) They are hardy to −30 degrees Fahrenheit.

(c) They all have refined new leaf shapes and colors.

(d) They all have thick, new flowers with new colors that bloom from the top to the bottom of the plant until frost. But, Satellite is more miniature in statue of leaves and plant.

Origin: A selected seedling from stated cross.

Type of plant: Hardy, herbaceous perennial.

Classification: Variety of hardy *Hibiscus* plant.

Propagation: Relatively easy to propagate by cuttings in approximately 2 weeks; holds its distinguishing characteristics through successive cuttings and divisions.

Size: About 2-2½ feet tall and about 2 feet wide.

Form: Symmetrical annual growth from perennial roots.

Habit: Upright and uniformly branched.

Growth: Vigorous; medium and compact. Full grown (2½ ft) in 2 years. 2 ft 5 inches when measured.

Hardiness: Hardy to at least −30 degrees Fahrenheit.

General health: Plant is very disease resistant against rot, aphids, spider mites, scale, white fly etc.; sturdy through excessive drought, rain or wind.

Foliage:

1. *Arrangement*.—Alternate.
2. *Shape*.—Juvenile: 3-5 lobed "maple-shaped" leaves. Rounded base shape. Mature: Small refined, "maple-shaped", 3-5 lobed leaf with entire to very mildly serrate margins and acute apices; rounded base.
3. *Size*.—Mature leaf (petiole base to apex): Length is about 5½ inches or 14 cm, width is about 4½ inches or 11.5 cm.
4. *Color*.—Young leaves (upper side)147 A: (purple cast) N 77A. Mature leaves: (upper side): 147 A, (purple cast) N 77A. Lower Leaf Veins: 61-A. Venation pattern: Palmate. Upper Leaf Venation color: N 77 A. Coloration of the mature lower leaf surface: Closest to; a little lighter than 146 B.
5. *Surface texture*.—Low sheen. Upper: Smooth. Lower: Semi-smooth.
6. *Petiole length*.—About 2.56 inches or 6.5 cm. Petiole diameter: 2 cm.
7. *Petiole color*.—146 B. Surface Texture: Semi-smooth.

Stems: The stems are stout at the base, becoming more slender toward the apices; coloration is consistent with the petiole. Length: 2-3 inches on average. Diameter: 2 cm. Internode length: 2 inches on average. Stem texture: Semi-smooth. Stem color: 147 B.

Blooming period: Profuse from July until frost (North, Midwest and Eastern U.S.); Profuse May or June until frost (Southwest and Southeast).

Flower diameter: Medium; about 8.46 inches or 21.5 cm.

Borne: Singly in the leaf axils, from midpoint of stems upward.

Bloom duration: Individual bloom lasts at least one full day; possibly up to 3 days.

Form: Campanulate; and overlapping.

Average number of flowers per season: 300.

Bud:

1. *Length*.—About 2 inches or (5 cm) on day before opening. Diameter: 1-2 inches.
2. *Color*.—182-B, 50-B and N 66-D.
3. *Surface texture*.—Semi-glabrous.
4. *Duration*.—One to two weeks.

Corolla: Having five petals 9-10½ inches across.

1. *Petal character and dimensions*.—Campanulate and very overlapping. (a) Length: About 3.35 inches or 8.5 cm. (b) Width: About 4.13 inches or 10.5 cm.
2. *Coloration*.—Rosy red-purple. (a) Bright red-mauve petals: Blend of 50-A (edges), N 66-C (mid-petal) and 65-D (veins upper and lower surface). Coloration of lower petal surface: 50-B and 182-C. (b) Venation in petals: 65-D. (c) Eye zone: 50-A.
3. *Texture*.—Shiny and smooth.
4. *Substance*.—Thick.
5. *Shape*.—Campanulate and very overlapping.

Reproductive organs:

1. *Staminal column*.—Stamen along basal two-thirds. Filament (anthers) length: 1¼"; 3.175 cm. Staminal column average length: About 1.85 inches or 4.7 cm. Stamen color Designation: 69-C. Average number of stamen per flower: 100. Pollen color: 12-D.
2. *Style*.—Terminates upper one-third of staminal column. Length: ½". Stigmatic lobe color (style color): N 66-D and 69-C. Stigma average size: ½"; 1.27 cm.

Calyx: Connate at the base; about 1.77 inches or (4½ cm) in length. Average 1 per flower. Upper and Lower Color: Between 146-A and 146-B. Shape: 5 lobed, connate at base. Surface Texture: Smooth.

Stipules: None.

Epicalyx: Whorl of bracts.

1. *Shape*.—10-12 slender, sword-shaped bractlets.
2. *Length*.—About 1.89 inches or (4.8 cm).
3. *Color upper and lower surface*.—177-A.

Peduncle:

1. *Length*.—About 1.97 inches or (5 cm).
2. *Strength*.—Stiff and sturdy.
3. *Color*.—Light to medium green with slight reddish-purple cast. 146-A with 61-C. Texture: Semi-smooth.

Seeds (fruit): Size: 1 cm. Color: Grey-brown. Average number: Less than 100.

The invention claimed is:

1. A new and distinct cultivar of hardy *Hibiscus* plant, as herein shown and described, characterized by its compact nature, refined petite, glabrous "maple-like" foliage of a purple coloration, its medium rosy-mauve flowers, its vigor and its hardiness.

* * * * *